United States Patent [19]

Fujioka et al.

[11] Patent Number: 5,236,704
[45] Date of Patent: Aug. 17, 1993

[54] CONTROLLED RELEASE FORMULATION

[75] Inventors: Keiji Fujioka, Amagasaki; Shigeji Sato, Ibaraki; Nobuhiko Tamura, Toyonaka; Yoshihiro Takada, Takatsuki; Yoshio Sasaki, Toyonaka; Miho Maeda, Osaka, all of Japan

[73] Assignee: Sumitomo Phamraceuticals Co., Ltd., Osaka, Japan

[21] Appl. No.: 302,476

[22] Filed: Jan. 27, 1989

[30] Foreign Application Priority Data

Jan. 28, 1988 [JP] Japan .................................. 63-020459

[51] Int. Cl.$^5$ ...................... A61K 37/02; A61K 37/43; A61K 37/48; A61K 37/66
[52] U.S. Cl. .................................. 424/85.1; 424/85.2; 424/85.4; 424/94.1; 424/94.63; 424/94.64; 424/468; 514/2; 514/8; 514/12; 514/21; 514/784; 514/801; 514/964
[58] Field of Search ...................... 514/2, 21, 963, 964, 514/969, 970, 774, 784, 801, 21, 12, 8; 424/457, 468, 489, 499, 456, 460, 85.1, 85.2, 85.4, 94.1, 94.63, 95.64; 604/890.1

[56] References Cited

U.S. PATENT DOCUMENTS

| | | | |
|---|---|---|---|
| 4,164,559 | 8/1979 | Miyata et al. | 424/14 |
| 4,294,241 | 10/1981 | Miyata | 128/156 |
| 4,347,234 | 8/1982 | Wahlig et al. | 424/15 |
| 4,409,332 | 10/1983 | Jefferies et al. | 435/188 |
| 4,711,782 | 12/1987 | Okada et al. | 514/963 |
| 4,774,091 | 9/1988 | Yamahira et al. | 424/426 |
| 4,816,568 | 3/1989 | Hamilton, Jr. et al. | 530/399 |
| 4,849,141 | 7/1989 | Fujioka et al. | 424/457 |

FOREIGN PATENT DOCUMENTS

| | | |
|---|---|---|
| 0037943 | 10/1981 | European Pat. Off. . |
| 0082481 | 6/1983 | European Pat. Off. . |
| 0138216 | 4/1985 | European Pat. Off. . |
| 0139286 | 5/1985 | European Pat. Off. . |
| 0140255 | 5/1985 | European Pat. Off. . |
| 0230647 | 8/1987 | European Pat. Off. . |
| 0284039 | 9/1988 | European Pat. Off. . |
| 0292988 | 11/1988 | European Pat. Off. . |
| 3409372 | 9/1985 | Fed. Rep. of Germany ........ 514/12 |
| 56-122317 | 9/1981 | Japan . |
| 59-7684 | 2/1984 | Japan . |
| 59-19925 | 5/1984 | Japan . |

OTHER PUBLICATIONS

Remington Pharmaceutical Sciences; 15th Ed. (Mack Publishing Co. Easton, Pa.), pp. 1419-1420 (1975).

Primary Examiner—Jeffrey E. Russel
Attorney, Agent, or Firm—Birch, Stewart, Kolasch & Birch

[57] ABSTRACT

A controlled release formulation which comprises a compound selected from the group consisting of organic acidic compounds and acid anhydrides or esters capable of generating one of the organic acidic compounds through hydrolysis together with an active ingredient and collagen as a carrier, said formulation being capable of exhibiting a predetermined release profile of the active ingredient. A process for producing said formulation is also provided.

20 Claims, 4 Drawing Sheets

CONTROLLED RELEASE FORMULATION

The present invention relates to a controlled release formulation. More particularly, it relates to a controlled release formulation for human or veterinary use, which can control the release profile of an active ingredient contained therein.

Sustained release formulations, which release an active ingredient over a long period of time, have been recognized to be useful in various aspects: increase of therapeutical effect due to prolonged retention of an active ingredient over effective level in the blood; decrease of side-effects by reducing the maximal blood level of the active ingredient; simplification of administration methods and reduction of patient's pain due to a decrease of administration frequency.

Various polymers are known to serve as a carrier material for preparing sustained release formulations. Examples of polymers employable in sustained release formulations are vinyl polymers, silicones, polyvinylalcohols, polypeptides, chitosan, collagen, polylactic acid, polyglycolic acid, and the like. Among them, polypeptides, chitosan, collagen, polylactic acid, and polyglycolic acid are preferable because they are biodegradable. Above all, collagen, which is a protein constituting one third of the total proteins in mammals, is highly biocompatible and is considered a most preferred carrier. The inventors of the present invention recognized such usefulness of collagen, and succeeded in producing sustained release formulations using the same as a carrier matrix. See Japanese Patent Publication (Kokai) Nos. 126217/1985, 97918/1985, 84213/1985, 89418/1985, 112713/1985, 236729/1986, and 230729/1987.

However, the release of an active ingredient cannot be adjusted in the desired manner with the sustained release formulations disclosed in the above publications, although they successfully attain sustained release of an active ingredient. Accordingly, an extended study is necessary in order to prepare the above-mentioned formulations in which the release rate or release profile of an active ingredient is suitably controlled. Such controlled release becomes necessary when the disease to be treated, the nature of an active ingredient to be used or the duration of administration of the formulation requires a particular release rate or release profile.

In view of the above, the inventors of the present invention continued the study looking for an ideal controlled release formulation which permits arbitrary control of the release rate or release profile, and found that an addition of a predetermined amount of an organic acidic compound as an additive to a sustained release formulation comprising collagen and an active ingredient allowed suitable control of a release rate or release profile of the active ingredient. The present invention has been completed on the basis of this finding.

Thus, the present application provides a controlled release formulation comprising an active ingredient and collagen as a carrier, the improvement comprising rising in the formulation a compound selected from the group consisting of organic acidic compounds and acid anhydrides or esters capable of generating one of said acidic compounds through hydrolysis.

The present application also provides a process for preparing a controlled release formulation comprising an active ingredient and collagen as a carrier, said formulation exhibiting a predetermined release profile of the active ingredient, which process is characterized in that a compound selected from the group consisting of organic acidic compounds and acid anhydrides or esters capable of generating one of the acidic compounds through hydrolysis is incorporated into the formulation during the production process thereof.

The present application further provides a method for controlling the release rate or release profile of an active ingredient from a sustained release composition comprising collagen and said active ingredient, characterized in that said composition comprises additionally a compound selected from the group consisting of organic acidic compounds and acid anhydrides or esters capable of generating one of the organic acidic compounds through hydrolysis.

The term "organic acidic compound" herein employed denotes a pharmaceutically or veterinarily acceptable organic compound, an aqueous solution of which shows a pH of less than 7. Examples of such organic compounds are organic compounds possessing one or more carboxylic groups, such as citric acid, tartaric acid, succinic acid, acetic acid, etc.; and amino acids such as aspartic acid, glutamic acid, glycine, alanine, etc. which show a pH of less than 7 when dissolved in water in spite of bearing a basic functional group or groups. Other compounds which are free from carboxylic groups but show a pH less than 7 when dissolved in water, such as ascorbic acid, are included in organic acidic compounds according to the present invention. Citric acid, among them, is most preferred.

Acid anhydrides or esters capable of generating the acidic compound through hydrolysis can be employed in lieu of the above-mentioned organic acidic compounds. Examples of the anhydrides or esters are succinic anhydride, glutamic anhydride, isocitric acid lactone, etc. The organic acidic compounds and the acid anhydrides or esters capable of generating one of the acidic compounds will hereinafter collectively be referred to as "acidic compounds" for simplicity.

The controlled release formulation of the invention may contain a single acidic compound. However, two or more acidic compounds listed above may be employed in the formulation of the invention.

The content of the acidic compound(s) in the formulation varies depending on the nature of the acidic compound(s) to be used and the release rate or release profile to be attained. In general, the amount of the acidic compound(s) to be added ranges from 1 to 50% by weight in terms of the total weight of the formulation.

Specifically, the preferable amount of citric acid, alanine and glycine to be added is about 5-50%, 5-50%, and 5-45% by weight respectively.

More specifically, addition of about 5-20% by weight of citric acid or about 5-30% by weight of glycine is especially preferred where the active ingredient is a growth hormone-releasing factor, about 5-20% by weight of weight of citric acid or about 5-30% by weight of glycine is especially preferred where the active ingredient is an interferon, and about 5-20% by weight of citric acid is especially preferred where the active ingredient is calcitonin. As far as the above active ingredients are concerned, the amount of the active ingredient released during a given period of time can be increased by increasing the amount of an organic acidic compound to be added.

Collagen employed in the formulations of the invention as a carrier is a substance which is found widely in animals. It constitutes one third of total proteins of mammalians. According to a recent finding, collagen has many variations. For instance, it is known that there are 10 or more variations of collagen in mammalians and birds, which differ from each other in the genetic point of view, and are classified into Type I to Type X. Preferred collagen employed according to the present invention is of Type I and of mammalian origin, although other collagens are employable.

Collagen is known to be compatible with animal tissue or organ and has widely been used as a surgical suture in medical operations. However, for securing complete safety, there may be employed atelocollagen which has far less antigenicity and which is obtained by removing telopeptide regions from the collagen molecules.

There is no limitation as to the active ingredient employable in the controlled release formulation of the present invention, and various bioactive substances such as prostaglandins, prostacyclines, vitamins, steroids, proteins and peptides are illustrated as the active ingredient. However, the formulations of the invention are most suitable in those which contain an active ingredient that is usually employed in an aqueous solution and in a very small amount in clinical use. Most preferred ingredients are bioactive proteins and peptides such as cytokines, hormones, hormone releasing factors, hormone-release inhibiting factors, growth factors, enzymes and the like.

Cytokine is a general term for bioactive and soluble substances which are released from macrophages or lymphocytes when they are stimulated by antigens or mitogens. Cytokine produced by lymphocytes is referred to as lymphokine and that produced by macrophages or monocytes is called monokine. There is no limitation to cytokines employable in the formulation of the invention and exemplified by interferon (IFN), interleukin (IL), colony-stimulating factor (CSF), macrophage activating factor (MAF), and macrophage migration inhibiting factor (MIF). The term "interferon" herein used denotes any type of interferons including $\alpha$-, $\beta$-, and $\gamma$-interferons, etc., as well as a blend thereof. Likewise, interleukin includes IL-1, IL-2, IL-3, etc., and colony-stimulating factor includes multi-CSF, granulocyte-monocyte macrophage CSF (GM-CSF), granulocyte CSF (G-CSF), monocyte macrophage CSF (M-CSF), etc., and a mixture thereof.

Hormones are substances which are produced in, and secreted from, a particular cell in response to biological interior or exterior information, and convey the information to another cell, i.e., a target cell for hormone, through body fluid. There is no limitation to the hormones employable in the formulation of the invention and illustrated by growth hormone (GH), calcitonin (CT), and the like.

Hormone-releasing factors are substances which cause secretion of hormones by direct action to endocrine glands. Examples of hormone-releasing factors employable in the formulation of the invention are growth hormone-releasing factor (GRF), luteinizing hormone-releasing factor (LH-RI), and the like, although the factors are not limited thereto. GRFs are peptides which have an ability of stimulating growth hormone secretion and those consisting of 44, 40, 37 and 29 amino acids are known to be active. Any of these GRFs and a mixture thereof can be employed according to the invention.

Hormone-release inhibiting factor, which is a substance inhibiting a release of hormone by direct action to an endocrine organ, is another example of the active ingredient employed in the present invention. Examples of hormone-release inhibiting factors are somatost-atin, melanostatin, and the like.

Growth factors are further examples of the active ingredient preferably employed in the formulation of the invention, which factors are substances defined as having an ability of promoting growth of animal cells both in vitro and in vivo but not belonging to nutrients. Typical growth factors are somatomedin (SM), nerve growth factor (NGF), epidermal growth factor (EGF), fibroblast growth factor (FGF), transforming growth factor (TGF), erythropoietin (EPO), platelet-derived growth factor (PDGF), and the like.

Above-mentioned somatomedin (SM) means any member of the somatomedin group, such as SM-A, SM-B, SM-C and further insulin-like growth factor (IGF)-I, (IGF)-II as well as MSA (multiplication stimulating activity). It is reported that SM-C is the same as IGF-I. Anyway, any of these peptides or a mixture of two or more thereof may be used in the present invention.

No limitation exists to enzymes employable in the formulation of the invention. Such enzymes are illustrated by thrombus lysing agent, such as tissue plasminogen activator (TPA), urokinase (UK), and the like.

The proteins and peptides specifically illustrated above under categories of cytokines, hormones, hormone-releasing factor, hormone-release inhibiting factors, growth factors, and enzymes include substances which cannot definitely and primarily be classified because of a variety of actions and origins thereof. The present invention can be applied not only to the substances illustrated or categorized above, but also to other peptides, proteins and glycoproteins which are expected to become useful medicines in the future, such as an enzyme inhibitor (e.g. a collagenase inhibitor, tissue inhibitor of metalloproteinase (TIMP)), bone morphogenetic protein (BMP), a certain antibody, and the like.

The above proteins and peptides employed in the formulation of the present invention may come from any origin and may be obtained by extract from relevant tissue or organ, by chemical synthesis, or by recombinant DNA technology.

The skilled person in the art will easily understand that the formulation of the present invention can contain one or more of the active ingredients illustrated above.

The controlled release formulation of the invention can be produced by conventional methods except that the methods include an additional step of incorporating into other starting materials a predetermined amount of one or more acidic compounds so that the predetermined amount of the acidic compound(s) may control the release rate or release profile of an active ingredient in the manner as desired. For example, the formulation may be prepared by the following steps:

Lyophilizing a mixture comprising an active ingredient, collagen and an appropriate amount of acidic compound, pulverizing the resulting solid product, and compression-molding the pulverized product in a template, or charging the above-mentioned mixture in a template and condensing or drying the mixture, to obtain the formulation in a solid form, whereby any formulation having desired size and shape suitable for particular administration route and particular position to be applied can be obtained Specific examples of the shape of the formulation are bar-like, rod-like, needle-like, disk-like, film-like, and spherical shape. The aforementioned mixture can also be blended and kneaded in the presence of an appropriate amount of water or buffer, and subjected to injection-molding followed by drying to prepare a needle-like or bar-like shaped formulation. In the latter method, collagen which exhibits acidic to neutral pH may be employed because collagen has a fiber-forming property under condition of basic to neutral pH.

The above methods do not require a binding agent, heat and organic solvents, and therefore, the methods are especially suitable for the preparation of the formulation containing an active ingredient which is unstable under existence of the above factors.

The specific embodiments for producing the formulation of the invention are presented above by way of illustration and should not be construed as limiting thereto in any respect.

The sustained release formulation of the invention can be administered to a living body through any one of conventional methods. However, a suitable administration route is parenteral administration, and injection, implantation, and insertion or implantation during surgical operation are most preferred. Direct application of the formulation of the invention in a solid form produces an excellent therapeutical effect. Topical administration is most suitable with the formulation in the form of a film or a sheet. Thus, the formulation of the invention can be applied systemically or topically.

With the controlled release formulation of the invention, the release rate of an active ingredient can be adjusted as desired by virtue of the addition of an organic acidic compound. In addition, the carrier contained in the formulation is collagen which is highly biocompatible and biodegradable. Accordingly, the formulation of the invention is safe to use and especially suitable for the treatment of patients and animals.

The following detailed examples are presented by way of illustration of specific embodiments of the invention.

REFERENCE EXAMPLE 1

An aqueous solution containing 2 w/v % atelocollagen (21.25 ml) and an aqueous solution containing 10 mg/ml of growth hormone releasing factor (1-29) (GRF (1-29)) (7.5 ml) are uniformly admixed with care to prevent or minimize foam-generation, and the mixture is lyophilized. After the lyophilized material is added with distilled water and allowed to swell, the mixture is thoroughly blended in a mortar to obtain a uniform liquid mixture. The mixture is charged in a syringe and linearly extruded from the syringe through a nozzle. The extruded material is dried and cut into an appropriate size to obtain an acidic compound-free column-shaped formulation containing 15% by weight of GRF.

REFERENCE EXAMPLE 2

An aqueous solution containing 2 w/v % atelocollagen (16.6 ml) and an aqueous solution containing 10 mg/ml of human calcitonin (6.8 ml) are mixed well with care to prevent or minimize foam-generation. The resultant mixture is lyophilized, added with an appropriate amount of distilled water allowed to swell, and blended thoroughly in a mortar to obtain a uniform liquid mixture. The mixture is molded in a similar manner as in Reference Example 1 to obtain a column-shaped formulation containing 17% by weight of calcitonin, and no acidic compound.

EXAMPLE 1

Citric acid (25 mg) is added to an aqueous solution containing 2 w/v % atelocollagen (20 ml). The resultant solution and an aqueous solution containing 10 mg/ml of GRF (1-29) (7.5 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is charged in a syringe, linearly extruded therefrom through a nozzle, dried, and cut into an appropriate size. This gives a column-shaped formulation which contains 15% by weight of GRF and 5% by weight of citric acid.

EXAMPLE 2

Citric acid (50 mg) is added to an aqueous solution containing 2 w/v % atelocollagen (18.75 ml). The resultant solution and an aqueous solution containing 10 mg/ml of GRF (1-29) (7.5 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a column-shaped formulation which contains 15% by weight of GRF and 10% by weight of citric acid.

EXAMPLE 3

Citric acid (25 mg) is added to an aqueous solution containing 2 w/v % atelocollagen (23.75 ml). The resultant solution and an aqueous solution containing 20 MU/ml of α-interferon (2 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 and subsequently molded into a needle-like shaped product to give a needle-like formulation containing α-interferon and 5% by weight of citric acid.

EXAMPLE 4

Citric acid (100 mg) is added to an aqueous solution containing 2 w/v % atelocollagen (20 ml). The resultant solution and an aqueous solution containing 20 MU/ml of α-interferon (2 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a bar-like formulation containing α-interferon and 20% by weight of citric acid.

EXAMPLE 5

Citric acid (40 mg) is added to an aqueous solution containing 2 w/v % atelocollagen (14.6 ml). The resultant solution and an aqueous solution containing 10 mg/ml of human calcitonin (6.8 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a column-shaped formulation containing 17% by weight of calcitonin and 10% by weight of citric acid.

EXAMPLE 6

Aspartic acid (40 mg) is added to an aqueous solution containing 2 w/v % atelocollagen (15 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a column-shaped formulation containing 15% by weight of GRF and 10% by weight of aspartic acid.

EXAMPLE 7

Aspartic acid (80 mg) is added to an aqueous solution containing 2 w/v % atelocollagen (13 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed to swell, and blended and kneaded well in a mortar to obtain a uniform liquid mixture. The mixture is molded in the same manner as in Example 1 to give a cylindrical-shaped formulation containing 15% by weight of GRF and 20% by weight of aspartic acid.

EXAMPLE 8

Aspartic acid (160 mg) is added to an aqueous solution containing 2 w/v % atelocollagen (9 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a rod-like formulation containing 15% by weight of GRF and 40% by weight of aspartic acid.

EXAMPLE 9

Glutamic acid (20 mg) is added to an aqueous solution containing 2 w/v % atelocollagen (16 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 and subsequently subjected to a compression-molding to give a disk-like shaped formulation containing 15% by weight of GRF and 5% by weight of glutamic acid.

EXAMPLE 10

Glutamic acid (40 mg) is added to an aqueous solution containing 2 w/v % atelocollagen (15 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is molded in the same manner as in Example 1 to give a column-shaped formulation containing 15% by weight of GRF and 10% by weight of glutamic acid.

EXAMPLE 11

Glutamic acid (80 mg) is added to an aqueous solution containing 2 w/v % atelocollagen (13 ml). The resultant solution and an aqueous solution containing 10 mg/ml of GRF (1-29) (6 ml) are thoroughly admixed with care to prevent or minimize foam-generation. The mixture is lyophilized, added with an appropriate amount of distilled water allowed, to swell, and blended well in a mortar to obtain a uniform liquid mixture. The mixture is molded in the same manner as in Example 1 to give a column-shaped formulation containing 15% by weight of GRF and 20% by weight of glutamic acid.

EXAMPLE 12

An aqueous solution containing 10 mg/ml of glycine (7 ml) is added to an aqueous solution containing 2 w/v % atelocollagen (26.25 ml). The resultant mixture and an aqueous solution containing 10 mg/ml of GRF (1-29) (10.5 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is charged in a syringe, linearly extruded therefrom through a nozzle, dried, and cut into appropriate sizes. This gives a column-shaped formulation containing 15% by weight of GRF and 10% by weight of glycine.

EXAMPLE 13

An aqueous solution containing 10 mg/ml of glycine (21 ml) is added to an aqueous solution containing 2 w/v % atelocollagen (19.25 ml). The resultant mixture and an aqueous solution containing 10 mg/ml of GRF (1-29) (10.5 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is charged in a syringe, linearly extruded therefrom through a nozzle, dried, and cut into appropriate sizes. This gives a column-shaped formulation containing 15% by weight of GRF and 30% by weight of glycine.

EXAMPLE 14

An aqueous solution containing 10 mg/ml of citric acid (2.5 ml) is added to an aqueous solution containing 2 w/v % atelocollagen (20 ml). The resultant mixture and an aqueous solution containing 10 mg/ml of GRF (1-29) (7.5 ml) are thoroughly admixed with care to prevent or minimize foam-generation. The mixture is lyophilized, added with an appropriate amount of distilled water allowed to swell, and blended well in a mortar to obtain a uniform liquid mixture. The mixture is charged in a template and compressed to form a film, which is then dried and cut into an appropriate size to give a film-shaped formulation containing 15% by weight of GRF and 5% by weight of citric acid.

EXPERIMENT 1

Figure 1:
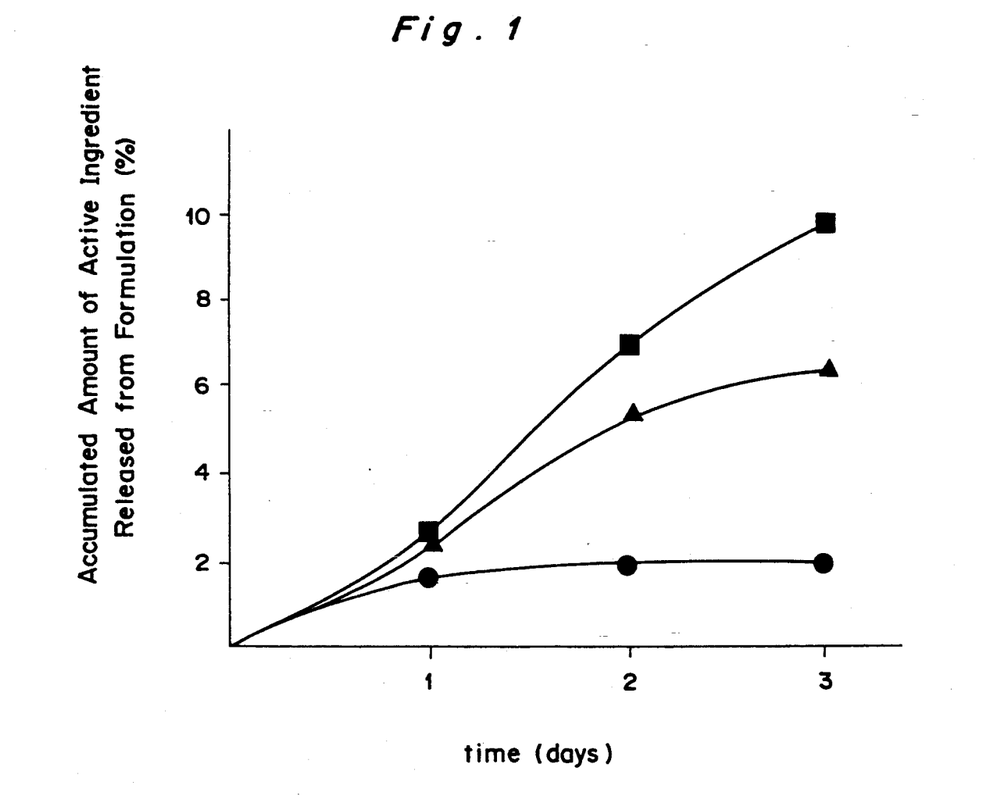
FIG. 1 of the accompanying drawings shows the time-course of the amount of GRF (1-29) released from the formulation of the invention during the release test in vitro (See Experiment 1). Vertical and horizontal axes show the accumulated amount of GRF released from the formulation and the time-course (days) respectively. The amount of GRF is indicated with the percentage (%) of the initial amount contained in the formulation. The symbols ▲, ■, and ● respectively represent the formulations obtained in Example 1, Example 2, and Reference Example 1.
Figure 2:
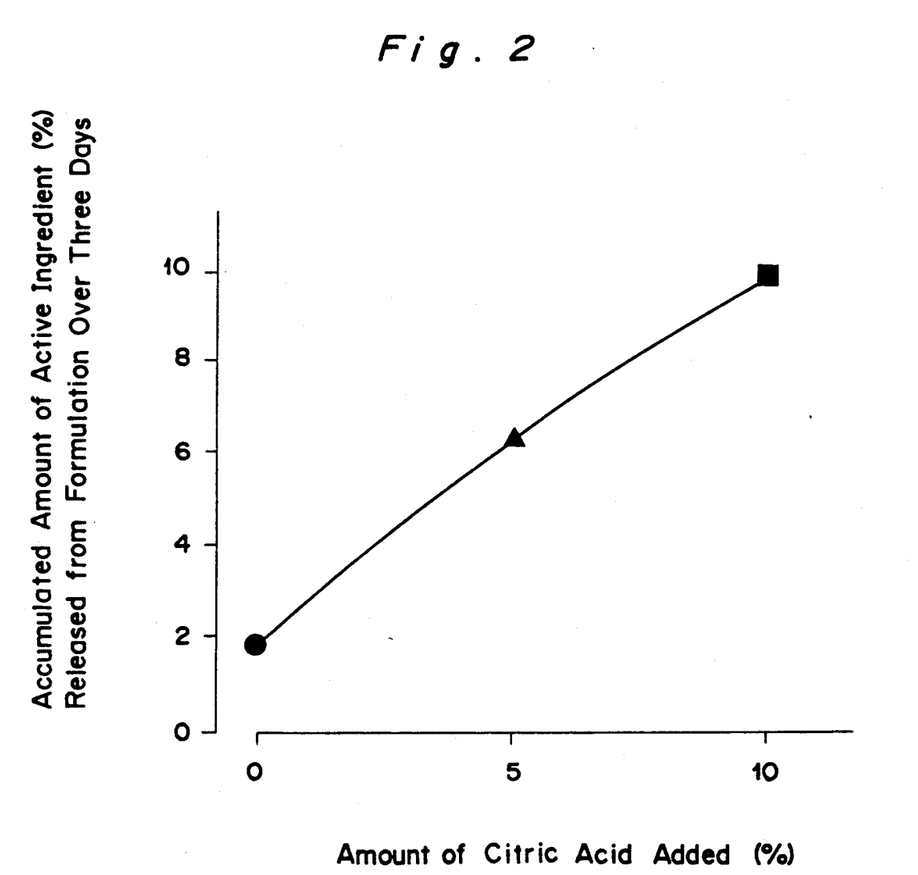
FIG. 2 shows the correlation between the accumulated total amount of GRF (1-29) released for three days from three different formulations obtained in Example 1, Example 2 and Reference Example 1 and the amounts of citric acid incorporated into respective formulations.

The column-shaped formulations obtained in Examples 1 and 2 and Reference Example 1, all of which contain GRF (1-29), were cut to obtain test samples of 10 mm length and subjected to a release test. Each of the samples was separately placed in 4 ml of a PBS(−) buffer solution, pH 7.4, and allowed to stand at 37° C. The amount of GRF (1-29) released into the solution from the formulation was measured by high performance liquid chromatography every day over three days, and the accumulated amount of GRF (1-29) released from the formulation was determined. The correlation among the accumulated amount of GRF released from the formulation, releasing time and the amount of acidic compound incorporated is shown in FIGS. 1 and 2 of the accompanying drawings.

EXPERIMENT 2

Figure 3:
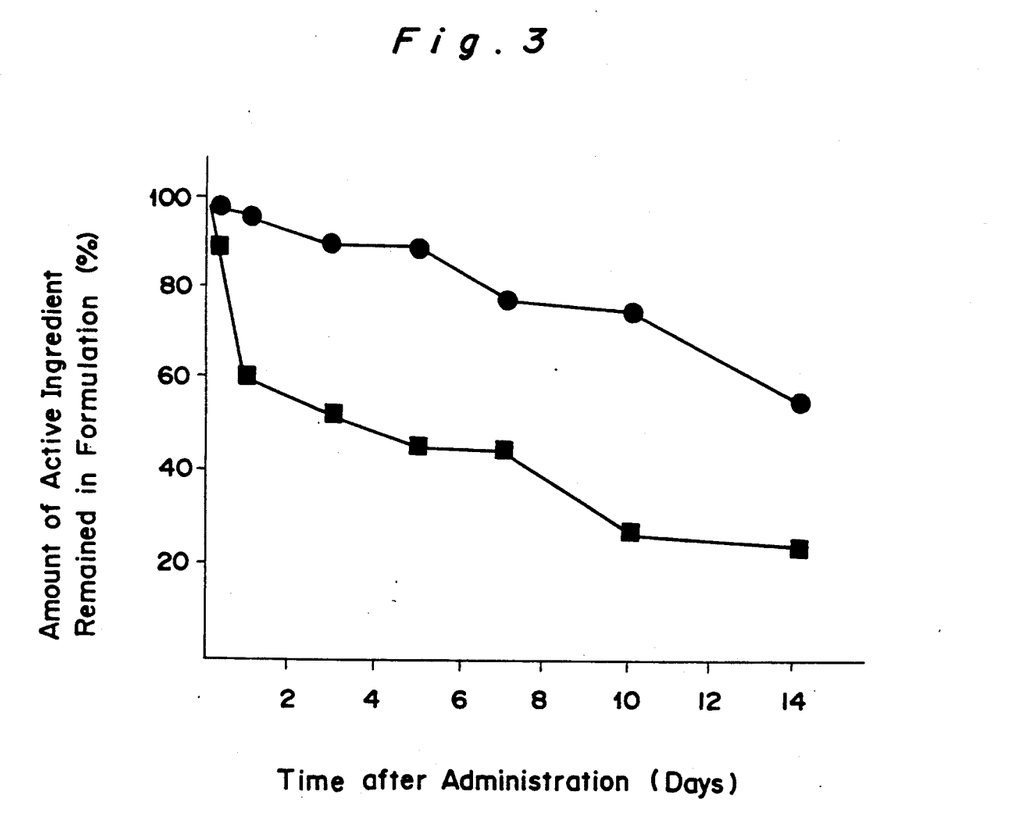
FIG. 3 shows the time-course of the amount of calcitonin remained in the formulations of the present invention after subcutaneous administration of the formulations in rats (See Experiment 2), wherein vertical and horizontal axes show respectively the residual amount of calcitonin in the formulation (%) recovered from the animal and the time-course (days) after administration, and the symbols ■ and ● represent the formulations obtained in Example 5 and Reference Example 2, respectively.

The column-shaped formulation obtained according to the method disclosed in Example 5 was subcutaneously administered to rats. The formulation obtained in Reference Example 2 was administered in the same manner as in the above and made a control. After administration, the residual calcitonin content in the formulation recovered from the animals was measured at intervals of one to four days for 14 days. The dosage was adjusted so that one rat receives 1.7 mg of calcitonin. The calcitonin content was measured by removing the formulation from the rats, immediately dissolving the recovered formulation into water, and subjecting the aqueous solution to high performance liquid chromatography. The test results are shown in FIG. 3.

EXPERIMENT 3

Figure 4:
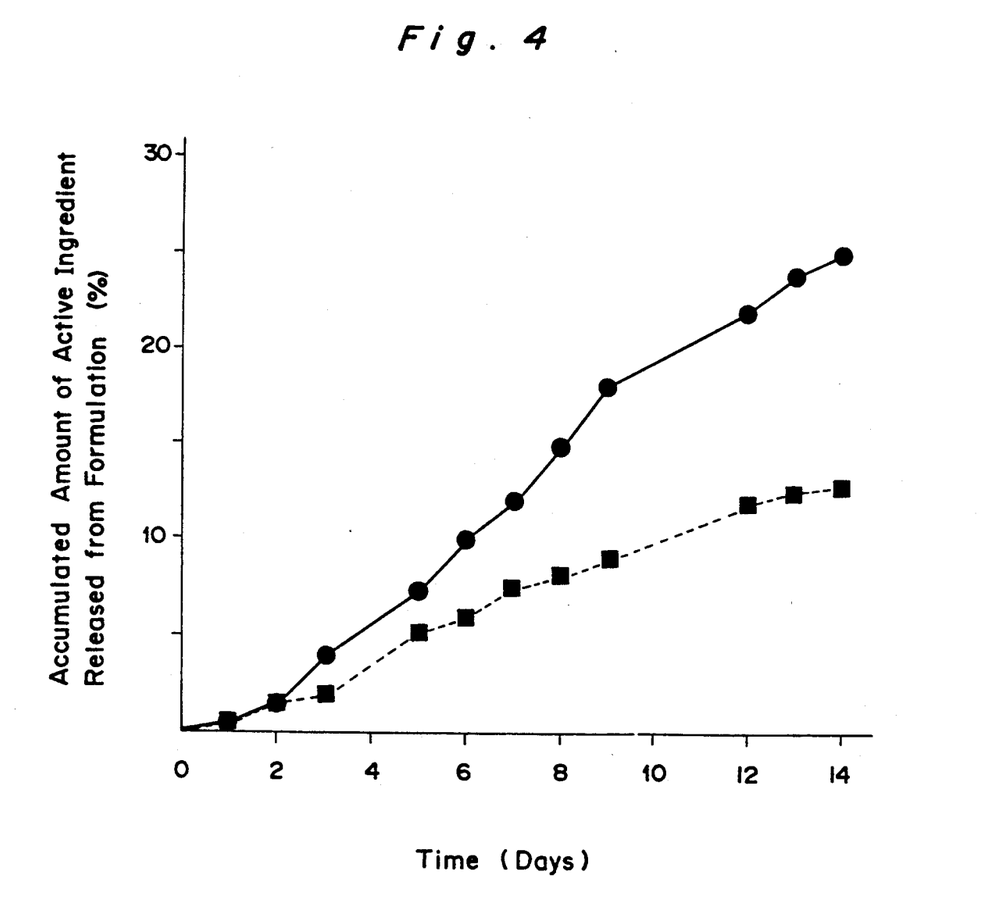
FIG. 4 shows the time-course of the accumulated amount of GRF (1-29) released from the formulations of the invention during Experiment 3, wherein vertical and horizontal axes show respectively the amount of GRF (1-29) released from the formulation and the time-course (days), said amount of GRF being indicated by percentage (%) of the initial amount. The symbols ■ and ● respectively show the formulations obtained in Examples 12 and 13.

GRF (1-29)-containing formulations obtained in Examples 12 and 13 were cut to obtain test samples of 10 mm length. Each of the samples was placed in 4 ml of PBS (−) buffer, pH 7.4, and allowed to stand at 37° C. The amount of GRF (1-29) released from each of the formulations was measured by means of high performance liquid chromatography, while totally replacing the buffer solution with fresh buffer solution after every sampling. The accumulated amount of GRF (1-29) released from each of the formulations is shown in FIG. 4.

The above in vitro tests described in Experiments 1 and 3 reveal that the release rate or release profile of an active ingredient contained in the formulations of the present invention is successfully controlled by the amount of an acidic compound incorporated into the formulation. Experiment 2, in vivo test in rats, also shows the usefulness of the addition of an acidic compound for the purpose of controlling the release rate of an active ingredient.

It was also observed in Experiment 2 that the degradation of collagen was accelerated by the addition of an acidic compound.

The above Experiments, as a whole, exhibit an excellent advantage possessed by the formulation of the invention in that the formulation will be able to meet every requirement concerned with a controlled release of an active ingredient, particularly in clinical use.

What we claim is:

1. A method for controlling the release rate or release profile of an active ingredient from a sustained release composition comprising collagen as a carrier and a bioactive protein or peptide as an active ingredient, which method comprises incorporating into the composition at least one amino acid in an amount of 1 to 50% by weight in terms of the total weight of the composition, said amino acid having a pH of less than 7 when dissolved in water and being incorporated into said composition to control the release rate or release profile of said active ingredient from said composition.

2. The method of claim 1, wherein said collagen is atelocollagen.

3. The method of claim 1, wherein the bioactive proteins and peptides are selected from cytokines, hormones, hormone-releasing factors, hormone release-inhibiting factors, growth factors and enzymes.

4. The method of claim 3, wherein the hormone-releasing factors are growth hormone-releasing factors and luteinizing hormone-releasing factor.

5. The method of claim 3, wherein the cytokines are selected from intereleukins, interferons, and colony-stimulating factors.

6. The method of claim 3, wherein the hormones are growth hormone and calctionin.

7. The method of claim 3, wherein the hormone release-inhibiting factor is somatostatine.

8. The method of claim 3, wherein growth factors are selected from the group consisting of somatomedin, nerve growth factor, epidermal growth factor, transforming growth factor, fibroblast growth factor, erythropoietin (EPO) and platelet-derived growth factor.

9. The method of claim 3, wherein the enzymes are tissue plasminogen activator and urokinase.

10. The method of claim 1, wherein the amino acid is a member selected from the group consisting of aspartic acid, glutamic acid, glycine, and alanine.

11. A method for controlling the release rate or release profile of an active ingredient from a sustained release composition comprising collagen and a hormone releasing factor ingredient, which method comprises incorporating into the composition at least one amino acid in an amount of 1 to 50% by weight in terms of the total weight of the composition, said amino acid having a pH of less than 7 when dissolved in water and being incorporated into said composition to control the release rate or release profile of said active ingredient from said composition.

12. The method of claim 11, wherein said amino acid is a member selected from the group consisting of aspartic acid, glutamic acid, glycine, and alanine.

13. The method of claim 11, wherein said collagen is atelocollagen.

14. The method of claim 11, wherein said amino acid is glycine.

15. The method of claim 13, wherein said amino acid is glycine.

16. The method of claim 11, wherein said hormone releasing factor is growth hormone releasing factor.

17. The method of claim 12, wherein said hormone releasing factor is growth hormone releasing factor.

18. The method of claim 13, wherein said hormone releasing factor is growth hormone releasing factor.

19. The method of claim 14, wherein said hormone releasing factor is growth hormone releasing factor.

20. The method of claim 15, wherein said hormone releasing factor is growth hormone releasing factor.

* * * * *

UNITED STATES PATENT AND TRADEMARK OFFICE
CERTIFICATE OF CORRECTION

PATENT NO. : 5,236,704
DATED : Aug. 17, 1993
INVENTOR(S) : Fujioka et al.

It is certified that error appears in the above-indentified patent and that said Letters Patent is hereby corrected as shown below:

Title page, item [73], Assignee:

Line 1, change "Phamraceuticals" to --Pharmaceuticals--

Line 2, after "Japan" add --and Koken Co., Ltd., Tokyo, Japan--

Signed and Sealed this

Twenty-sixth Day of April, 1994

Attest:

BRUCE LEHMAN

Attesting Officer

Commissioner of Patents and Trademarks